United States Patent [19]
Farnor, Jr. et al.

[11] Patent Number: 5,482,460
[45] Date of Patent: Jan. 9, 1996

[54] DENTAL MODEL ARTICULATOR

[75] Inventors: Robert P. Farnor, Jr., Erwin, Tenn.;
David G. Scruggs, Sommerville, Ala.

[73] Assignee: American Bictech, Inc., Erwin, Tenn.

[21] Appl. No.: 112,846

[22] Filed: Aug. 26, 1993

[51] Int. Cl.⁶ ................................................ A61C 11/00
[52] U.S. Cl. .................... 433/57; 433/60; 433/64
[58] Field of Search ..................... 433/54, 55, 56, 433/57, 58, 59, 60, 62, 64

[56] References Cited

U.S. PATENT DOCUMENTS

| | | | |
|---|---|---|---|
| 1,055,357 | 3/1913 | Robin | 433/60 |
| 1,587,821 | 6/1926 | Darcissac. | |
| 2,403,177 | 11/1947 | Johnson et al. . | |
| 3,059,336 | 10/1962 | Windish | 433/54 X |
| 3,067,515 | 12/1962 | Wilkinson | 433/60 |
| 3,097,431 | 7/1963 | Harris. | |
| 3,466,750 | 9/1969 | Timberlake et al. . | |
| 3,727,311 | 4/1973 | Schoonebeek. | |
| 3,823,476 | 7/1974 | Hudson et al. . | |
| 4,496,320 | 1/1985 | Hwang et al. . | |
| 4,548,581 | 10/1985 | Huffman . | |
| 4,786,253 | 11/1988 | Morais | 433/60 |
| 4,797,097 | 1/1989 | Cohn | 433/64 |
| 4,865,544 | 9/1989 | Scruggs | 433/64 |

FOREIGN PATENT DOCUMENTS 2139092  11/1984  United Kingdom ............. 433/54

Primary Examiner—Nicholas D. Lucchesi
Attorney, Agent, or Firm—Luedeka, Neely & Graham

[57] ABSTRACT

The specification discloses an articulator and associated method for assembling upper and lower dental models corresponding to the upper and lower sets of a patient's teeth in a desired occlusal relationship for simulation of occlusal and masticatory movements by application of a force to the dental models supported by the articulator. The articulator comprises a frame comprising resiliently deformable first and second frame sections pivotally connected together for pivotal movement about a pivot axis. Each of the frame sections includes an elongate channel, the channels being arranged such that pivotal movement of the frame sections about the pivot axis sweeps the length axes of the channels through arcs in a plane disposed substantially perpendicular to the pivot axis. Structure is provided for limiting pivotal movement of the frame sections beyond a closed position at which the length axes of the channels are disposed substantially coaxially. First and second protrusion members are provided for attachment to the first and second dental models, respectively, and are dimensioned to be received within the channels and adhesively secured thereto at desired positions along the length of the channels.

13 Claims, 8 Drawing Sheets

DENTAL MODEL ARTICULATOR

TECHNICAL FIELD

The present invention relates generally to dental prosthetics. More particularly the invention relates to a method and apparatus for supporting dental models in a manner which enables replication of normal mouth movements.

BACKGROUND

Well-known dental corrective techniques involve the replacement of a patient's teeth with artificial or false teeth. For example, a bridge is a type of dental corrective device which consists of one or more false teeth anchored between the patient's remaining teeth which abut the bridged site (known as "abutment teeth"), with the portion of the bridge that actually replaces the missing teeth being known as a pontic.

The bridge should be compatible with the patient's mouth in general and with the patient's other teeth to avoid discomfort and other problems. For example, when the teeth in a normal mouth are brought firmly together, the upper incisors (front teeth) should slightly overlap the lower incisors and the rest of the teeth should bite together with each upper tooth against its mate in the lower jaw and also against the lower tooth back of it. The bite is called occlusion. If the teeth do not bite together properly, the condition is called malocclusion and may interfere with masticatory movement (i.e., chewing) as well as with the symmetry of the face.

Rather than trial and error evaluation of a bridge in the patient's mouth, it is common to prepare a molded or cast dental model of both the upper and lower sets of teeth of the patient's mouth. The fit of the bridge is evaluated by use of the model and any necessary changes may be made to the bridge before installation of the bridge into the mouth of the patient. During evaluation of the bridge, it is desirable to study the compatibility of the bridge during both occlusal and masticatory movement of the dental model casts. To accomplish this, the dental model casts should be supported relative to one another in a manner which enables the simulation of the patient's mouth during occlusal and masticatory movement. Devices intended to provide such support are commonly known in the art as dental model articulators or correlators.

Known prior art articulators, particularly inexpensive ones, are disadvantageous in that they do not support dental model casts in a manner which approaches that of actual occlusal and masticatory movement of the jaw bone. Furthermore, because of the complex mouth movements which must be duplicated, many prior art articulators which are intended to more realistically reproduce mouth movement not only fall short of this goal but are complicated and expensive. Prior art articulators also are difficult to initially align and install on the dental model casts in a manner which duplicates the bite. This often results in poor alignment and reproduction of occlusion, and detrimentally affects reproduction of occlusal and masticatory evaluation of the bridge.

Variations of an inexpensive disposable articulator currently in use for relatively simple restorations are disclosed in U.S. Pat. Nos. 4,382,787 and 4,449,930 to Huffman. These devices use ball-and-socket joint interconnections between mounts on the upper and lower dental models and a resiliently flexible, hinged bracket. The ball-and-socket joints pivotably interconnect the hinged bracket with the casts to enable the technician to manipulate the casts into their proper bite registry or perform other functions which require a pivotable interconnection between the casts and their connected brackets. After the desired positioning is achieved the ball-and-socket joints are immobilized with an adhesive.

However, devices of the type shown in the '787 and '930 patents suffer from the disadvantage that the bracket and mount configuration often does not provide sufficiently firm or uniform resistance to masticatory movements of the dental models. Also, the twisting force in the assembled model is concentrated at the relatively narrow neck of the ball spaced from the hinges and the model or on the long arms of the brackets, so that a considerable lever or torque force may be concentrated upon the neck or bracket which may lead to mechanical failure of the device. In addition, variations in the vertical spacing between the ball-and-socket joints due to variations in the thickness or vertical dimension of the model casts may cause the hinge axis to be shifted rearwardly or forwardly in relation to the casts, depending on the thickness of the casts. This results in an unnatural variation in the location of the hinge or pivot axis because the axis is actually brought closer to the teeth for larger or thicker casts, while in nature the reverse may actually be the case in that the jaw pivot point is generally spaced farther from the teeth when they are larger.

SUMMARY OF THE INVENTION

Accordingly, it is an object of the present invention to provide an improved dental model articulator.

It is yet another object of the present invention to provide an improved method for assembling dental models with an articulator.

Yet another object of the present invention is to provide an articulator of the character described which enables more realistic reproduction of occlusal and masticatory movements.

A further object of the present invention is to provide an articulator of the character described which deforms in response to force applied thereto by a dental technician.

A still further object is to provide an articulator which more uniformly yieldably resists forces applied thereto by a dental technician.

An additional object of the invention is to provide a method of the character described which facilitates achievement of occlusion of cast models in an improved manner.

Another object of the invention is to provide an articulator which is inexpensive and disposable.

Still a further object of the invention is to provide an articulator which is disposable and provides an improved support for dental models to more firmly and uniformly support dental models in a manner which enables a technician to realistically and repeatably duplicate desired mouth movements.

Still another object of the present invention is to provide an articulator and associated method which is uncomplicated and which enables improved evaluation of bridges and other dental corrective devices as compared to conventional articulators and methods.

Having regard to the foregoing and other objects, features and advantages, the present invention is directed to an articulator for assembling upper and lower dental models in a desired occlusal relationship for simulating occlusal and masticatory movements. The articulator comprises a frame having a first resiliently deformable frame section, a second resiliently deformable frame section and structure for pivotably interconnecting the first and second frame sections for pivotal movement about a pivot axis.

Each of the first and second frame sections includes an elongate channel disposed so that pivotal movement of the sections about the pivot axis sweeps the length axes of the channels of the sections through arcs in a plane disposed generally perpendicular to the pivot axis. The first and second frame sections are limited against movement beyond a closed position at which the length axes of the channels are disposed substantially coaxially; i.e., along substantially the same axis.

The articulator further comprises a pair of protrusion members for attachment to the dental models, the protrusion members dimensioned to be received into the channels of the first and second sections to enable the protrusions to be adhesively secured to the frames at desired positions along the length of the channels with the frame sections in the closed position.

The protrusion members are preferably generally hemi or semispherical in configuration, and the elongate channels of the frame sections are preferably of a round-bottomed configuration with a generally uniform radius of curvature extending along the length thereof, which radius is about the same as that of the radius of curvature of the protrusion members so that the surface of the protrusion members are matingly received within the channels to establish substantially no more than an arcuate line of contact between each protrusion member and its associated frame section, which line is preferably less than about 180°.

In assembly of the upper and lower models using the articulator, the protrusion members are attached to the models as by an adhesive and, with the models in a desired occlusal relationship, are placed into the channels of the frame sections and attached thereto, also as by an adhesive, with the frame sections in the closed position to dispose the channels in generally coaxial relation, whereupon the dental models are assembled in occlusion for simulation of masticatory or other mouth movements by flexure of the resiliently deformable frame sections supporting the models.

In one embodiment, the first and second frame sections each comprise an integral construction generally U-shaped in cross-section to define a front wall and a back wall and a bridge extending between opposite adjacent ends of the front and back walls to support the front and back walls in opposed, generally parallel spaced-apart relation. The frame sections are constructed of a substantially rigid, resiliently deformable plastic to resiliently yieldably resist application of a force exerted thereon so that the spatial relationship of the front and rear walls may be altered about the bridge upon application of a force to the bracket, with the memory of the plastic returning the walls to their predetermined opposed relationship.

The rear walls of the brackets are hingedly connected to one another for movement about a first pivot axis, and abutting structure is defined on the front walls of the brackets for limiting movement of the brackets toward one another about the first pivot axis beyond the closed position to maintain the coaxial relationship of the channels.

The frames preferably further include webs at the ends of the channels adjacent the pivot axis for limiting flow of adhesive from the channels into the area between the frame sections to avoid undesired interadhesion of the frame sections when they are in the closed position with the channels aligned for adhesively receiving the protrusions.

In another aspect, the present invention provides a method for assembling a dental model for evaluation. The method includes providing a pair of dental casts corresponding to the upper and lower sets of teeth of a human mouth, each of the casts having a rear surface and providing an articulator having a frame comprising first and second frame sections hingedly connected together for pivotal movement about a hinge axis, each frame section having a channel therein oriented generally perpendicular to the pivot axis and movable about the pivot axis to a closed position at which the channels are in coaxial relation with a stop to limit movement of the frame sections beyond the closed position. Projecting protrusions are attached to the rear surface of the dental model casts, the protrusions dimensioned to be received into the channels. With the frame sections in the closed position, and the casts in proper occlusal relation, the protrusions are placed in the channels to attach the casts to the frames, as by an adhesive applied to the interface between the protrusions and the channels.

BRIEF DESCRIPTION OF THE DRAWINGS

The above and other features and advantages of the present invention will become apparent from the following detailed description when considered in conjunction with the accompanying drawings in which.

DETAILED DESCRIPTION OF A PREFERRED EMBODIMENT

Figure 1:
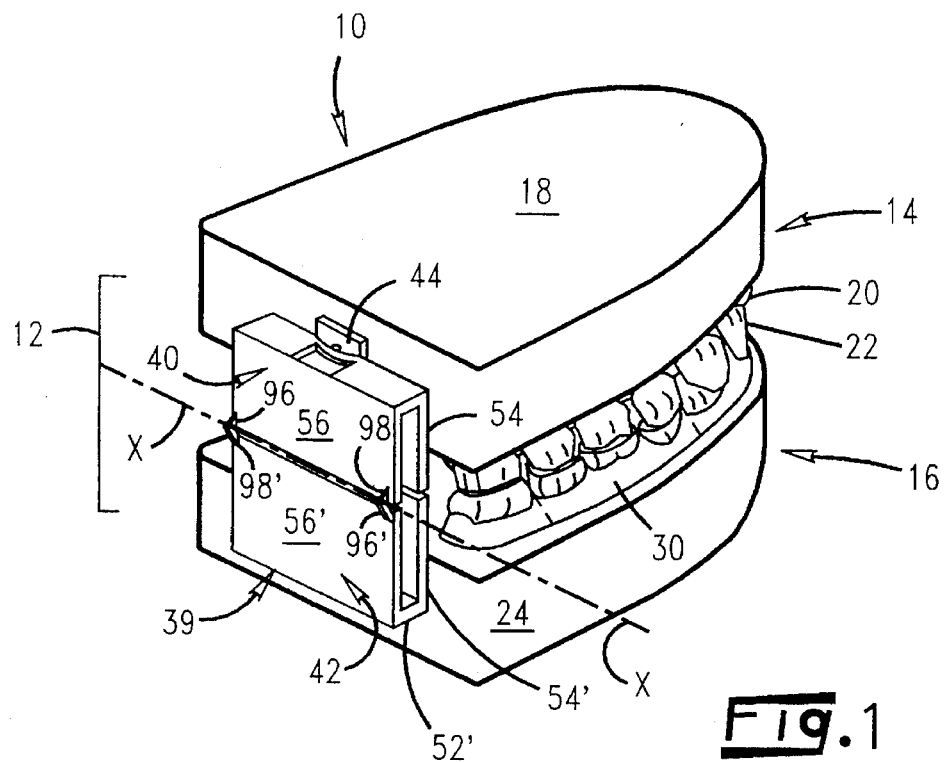
FIG. 1 is a rear perspective view of a dental model having a pair of dental casts supported by an articulator in accordance with the present invention.

Referring now to the drawings in which like reference characters refer to like or similar parts throughout the several views, FIG. 1 shows a dental model 10 assembled using an articulator 12 according to a preferred embodiment of the invention supporting an upper dental model cast 14 and a lower dental model cast 16 of a dental patient's upper and lower jaws, teeth and gums. The articulator 12 supports the casts 14 and 16 in a manner which enables improved simulation of occlusion and occlusal and masticatory movements of the casts 14 and 16, as will be explained more fully below.

As used herein, the term "occlusal movement" shall be understood to refer generally to movement of the model which brings the opposing surfaces of the teeth of the two jaws into contact from a spread apart position, wherein the term "occlusion" refers to the position of the teeth when the opposing surfaces of the teeth are in contact with one another in proper or desired bite registry. The term "masticatory movement" shall be understood to refer generally to a motion provided by the combination of vertical, horizontal and/or side-to-side movement of the teeth and jaws such as occurs when chewing with at least a portion of the upper teeth in contact with at least a portion for the lower teeth.

Figure 2:
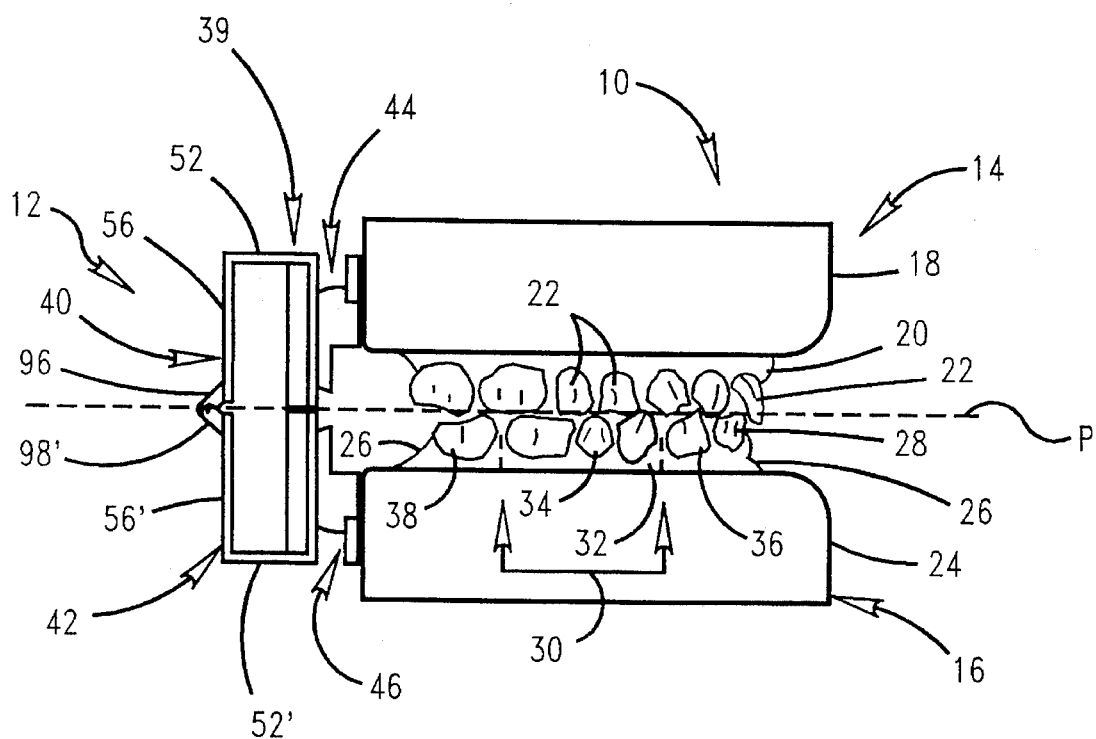
FIG. 2 is a side elevational view of the dental model of FIG. 1 with the teeth positioned in occlusion.

With reference now to FIG. 2, the cast 14 includes a jaw or base 18, gum 20 and teeth 22; and the cast 16 includes a jaw or base 24, gum 26, teeth 28, and a dental corrective device such as bridge 30. As mentioned previously, a bridge is a type of dental corrective device which consists of one or more false teeth anchored between the patient's remaining teeth which abut the bridged site. Accordingly, the bridge 30 may include an acrylic-resin base 32 and artificial teeth 34, and is removably positioned on the cast 16 between abutment teeth 36 and 38.

The fit of the bridge is evaluated by use of the articulator 12. During evaluation of the bridge, it is desirable to study the compatibility of the bridge during both occlusal and masticatory movement of the dental model casts. Accordingly, in FIG. 2, the casts 14 and 16 are shown supported by the articulator 12 with teeth 22 and 34 in occlusion. In this orientation, the dental technician may evaluate the bridge 30, particularly whether the teeth 34 are in occlusion or interfere with occlusion.

The articulator 12 of the present invention is advantageous over conventional articulators because it enables improved simulation of occlusal and masticatory movements of the casts 14 and 16 regardless of cast size and with reduced likelihood of mechanical failure. This provides a superior environment for evaluation of the bridge 30 or other dental corrective device and is thus helpful to provide a better fit of the bridge to the patient and reduce the likelihood of patient discomfort and other problems and costs associated with poor fitting bridges.

Figure 3:
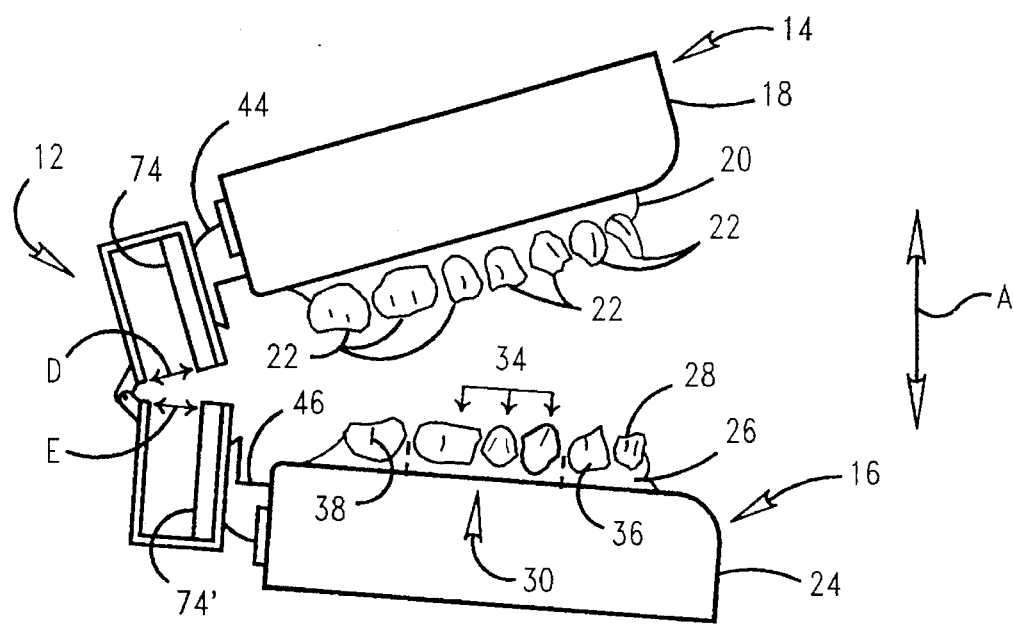
FIG. 3 is a side view of the model of FIG. 1 showing occlusal movement of the teeth.

To illustrate the nature of the occlusal and masticatory movement enabled by the articulator 12, FIG. 3 shows the casts 14 and 16 supported by the articulator 12 with teeth 22 and 34 spaced apart from one another, such as would occur during normal occlusal movement, indicated generally by the arrow A and effected by application of suitable external forces by the technician to the casts 14 and 16.

Figure 4:
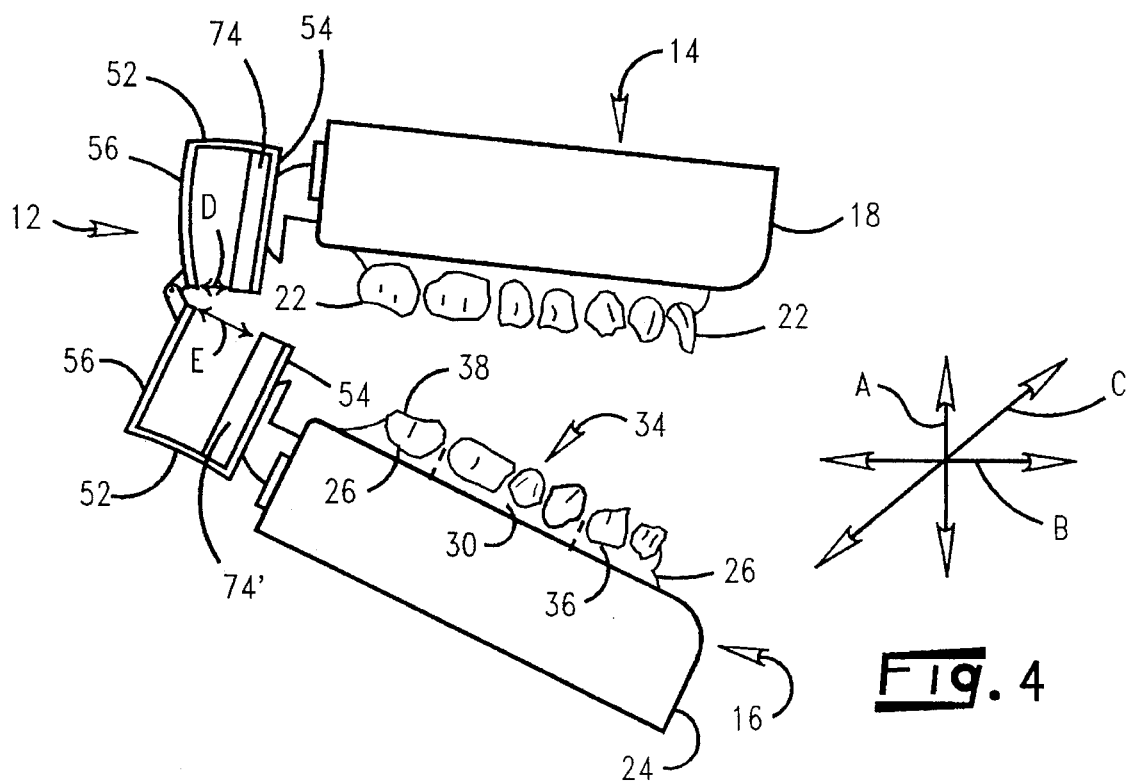
FIG. 4 is a side view of the model of FIG. 1 showing masticatory movement of the teeth.
Figure 5:
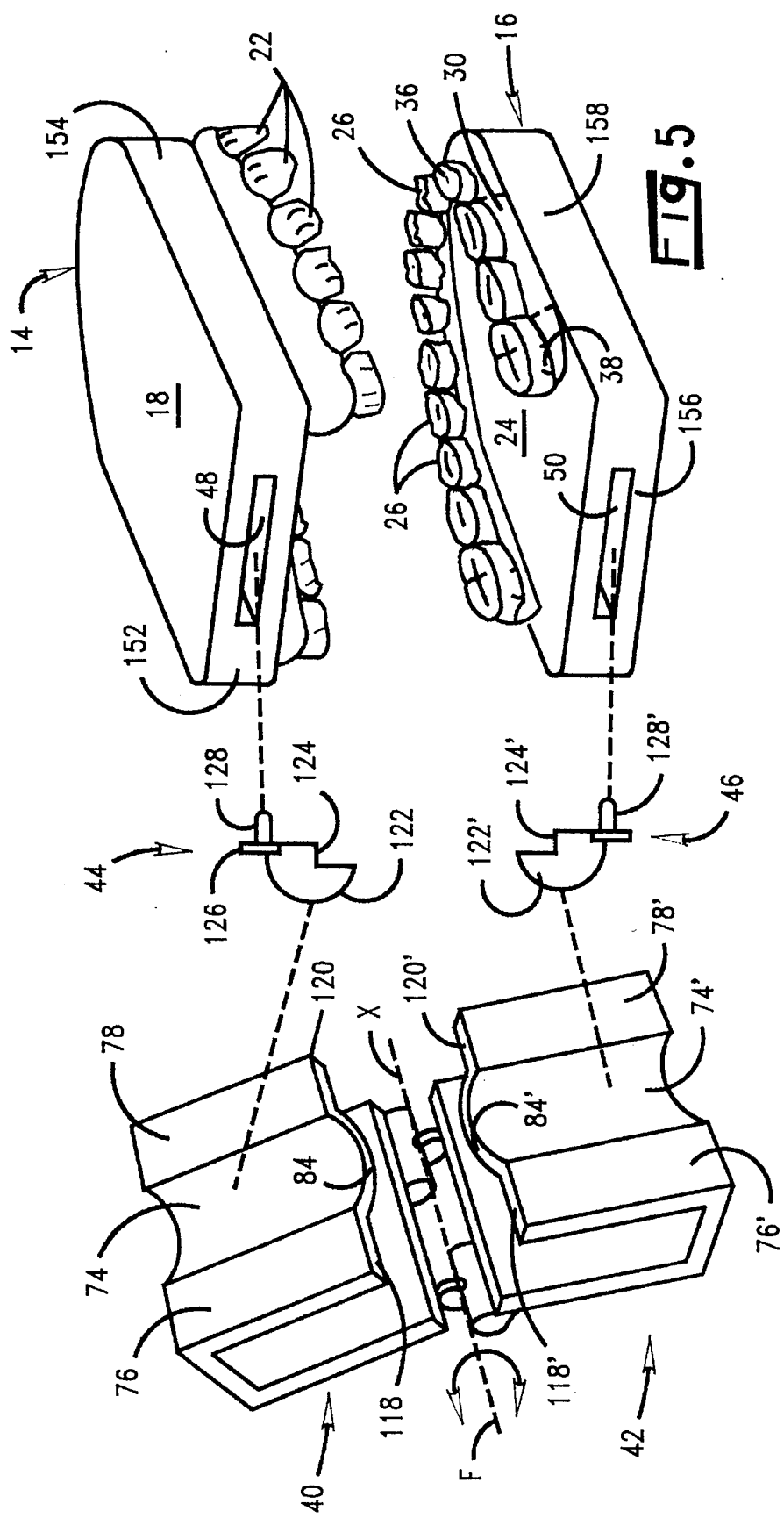
FIG. 5 is an exploded, enlarged view of the model of FIG. 1.

FIG. 4 shows the casts 14 and 16 supported by the articulator 12 with the teeth 22 and 34 spaced apart from one another with the teeth 34 also shifted laterally away from and forward of the teeth 22, such as would occur during normal masticatory movement, indicated generally by the arrow A and additional arrows B and C and effected by application of suitable external forces to the casts 14 and 16 such as would normally be applied by a dental technician when evaluating a dental corrective device.

Comparison of FIGS. 3 and 4 shows that the articulator 12 becomes deformed under application of forces to effect masticulatory movement. For example, the distance D is greater in FIG. 3 than in FIG. 4 and the distance E is less in FIG. 3 than in FIG. 4. As will be explained more fully below, the structure and size relationships of the components of the articulator provide for the depicted deformation and enables the articulator 12 to substantially uniformly resist the forces applied to the casts so that the movement imparted to the casts more realistically simulates occlusal and masticulatory movement of the human mouth. Additionally, this structure also enables the articulator to be used with casts of various sizes without affecting the spacing and with reduced likelihood of mechanical failure.

With reference now to FIGS. 1–5, the articulator 12 includes a frame 39 having an upper frame section 40 hingedly connected to a lower frame section 42 for rotation about pivot axis X and a pair of upper and lower protrusion members 44 and 46. As will be explained more fully below, the model is preferably assembled by adhesively securing the protrusion members 44 and 46 to the casts 14 and 16, respectively, and thereafter securing the protrusions 44 and 46 to the frame sections 40 and 42.

FIGS. 6a–6f show front, rear, left-side, right-side, top and bottom views, respectively, of the upper frame section 40. As shown, the frame section 40 may be a one piece molded plastic construction including a bridge panel 52 supporting front and rear panels 54 and 56 spaced apart from one another and extending downwardly from opposite sides of the bridge panel 52.

Figure 6A:
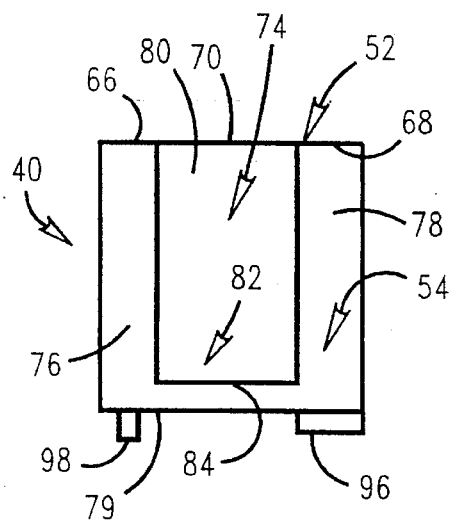
FIGS. 6a–6f are front, rear, left-side, right-side, top and bottom views, respectively, of a frame section of the articulator of the present invention.
Figure 6B:
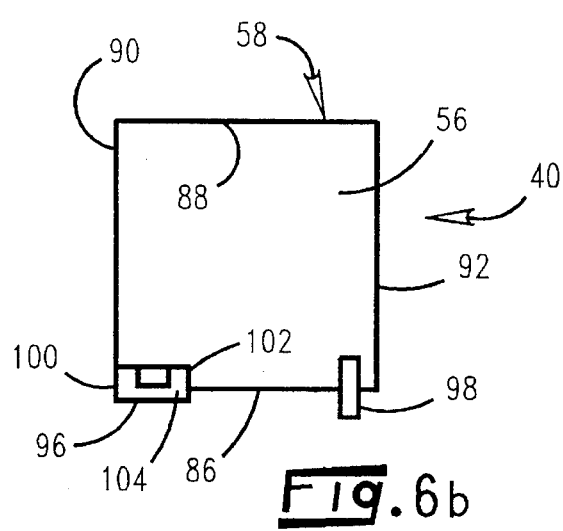
Figure 6C:
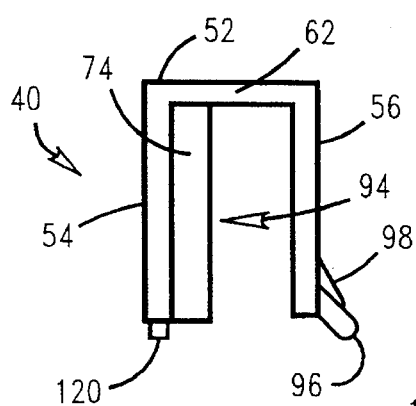
Figure 6D:
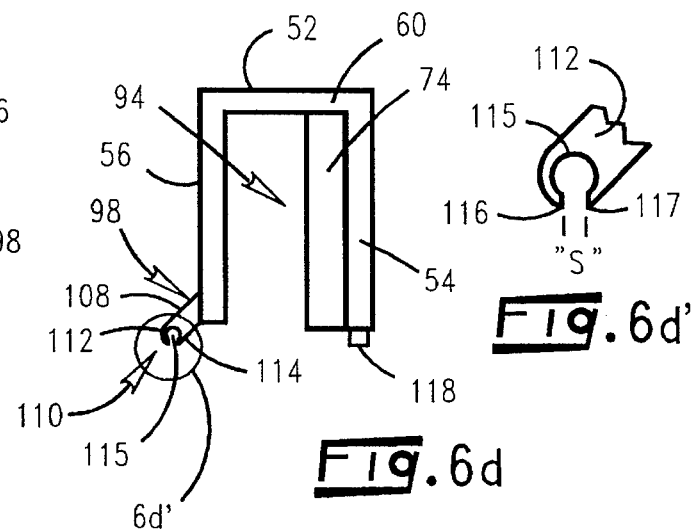
Figure 6E:
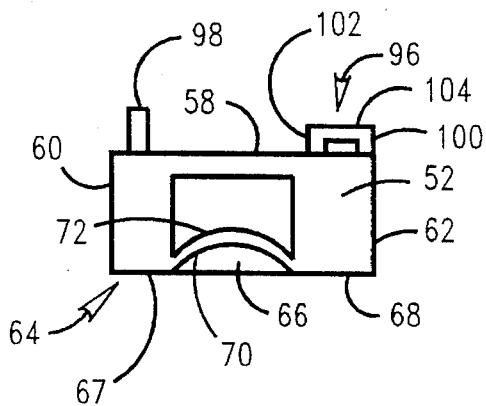

As best seen in FIG. 6e, bridge panel 52 may be substantially flat, having a thickness of about ⅛ inch and including a substantially straight rear edge 58 having a length of about 1 5/16 inches, parallel straight side edges 60 and 62, each having a length of about ½ inch and arranged perpendicular to the side edge 58 at opposite ends thereof, and a front edge 64. A saddle-shaped cut-out 66 is located intermediate side edges 60 and 62, adjacent front edge 64.

The front edge 64 includes straight segments 67 and 68 each having a length of about ⅜ inch and located on opposite sides of an arcuate edge 70 having a radius of curvature of about 3/10 of an inch as viewed in FIG. 6e. The cutout 66 is substantially rectangular, having a length of about ½ inch and a width of about ¼ inch, except for an arcuate front edge 72, which is spaced uniformly from the arcuate section 70.

The arcuate section 70 forms the top edge of an elongate, concave, cylindrical recess or channel 74, (FIGS. 6a and 6f) of the front panel 54, as will be explained below, and the arcuate section 72 of the cutout 66 is spaced apart from the arcuate section 70 by the thickness of the front panel 54, which is also about ⅛ inch.

The front panel 54 has flat rectangular faces 76 and 78 located on opposite sides of the channel 74, each face 76 and 78 having a length or height of about 1 inch and a width of about ⅜ inch and bounded on their ends adjacent bridge panel 52 by front edge 64 thereof, and bounded on their free ends by edge 79. The channel 74 has a length or height of about 15/16 inch and a depth or radius of about 3/10 inch. The channel 74 has an open upper end 80 adjacent the middle panel 52 and a lower end 82 adjacent end edge 79 provided by a web in the form of a circular segment 84 having a thickness of about 1/16 inch and configured to close the lower end of the channel 74 along end edge 79 adjacent pivot axis X.

The rear panel 56 (FIG. 6b) defines a substantially flat, rectangular surface having a lower free end edge 86 spaced and parallel to an upper edge 88 which coincides with straight rear edge 58 of the bridge panel 52. The rear panel 56 further includes parallel and opposite side edges 90 and 92. The rear panel 56 is supported in spaced apart substantially parallel relation to the front panel 54 by the bridge panel 52. This spaced apart relationship defines a generally U-shaped open area 94 between the panels 52, 54 and 56 as viewed from the side (FIGS. 6c and 6d).

The rear panel 56 includes a male hinge component 96 extending downwardly and outwardly therefrom adjacent one corner of the panel 56 defined by one end of the lower edge 86 and the side edge 90, and also includes a female hinge component 98 extending downwardly and outwardly therefrom adjacent the corner of the panel 56 defined by the other end of lower edge 86 and the other side edge 92. Of course, the placement of hinge components 96 and 98 may be reversed.

Figure 6F:
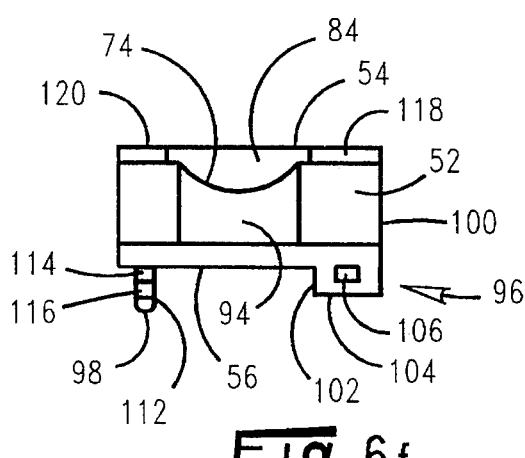

The male hinge component 96 includes a pair of spaced apart and parallel arms 100 and 102 which extend downwardly and outwardly from the panel 56. Each arm 100 and 102 has a length of about 1/4 inch, a width viewed from the side which tapers from about 1/8 inch adjacent the panel 56 to about 1/12 inch at its terminal end, a thickness viewed from the bottom of about 1/12 inch, and are disposed generally parallel to one another in spaced-apart relation at a spacing of about 1/8 inch. A cylindrical rod or post 104 having a diameter of about 1/12 inch extends between the terminal ends of the posts 100 and 102 to provide a substantially rectangular opening 106 as viewed from the bottom (FIG. 6f).

The female hinge component 98 (FIG. 6d) is provided by a projecting arm 108 having a lower end 110 which defines a pair of spaced-apart jaws 112 and 114. The jaws together define an opening 115 having a diameter of about 1/16 inch to engagingly receive a rod of the size and shape similar of the rod 104, as will be explained more fully below. As shown in FIG. 6d, it is preferred that the spacing between the outer ends of jaws 112 and 114, shown as separation "S", be slightly less than the diameter of the opening so that placement of a rod as in the rod 104 therein is achieved by a snap-fit to firmly and rotatably support rod 104 therein. Thus, urging of a rod of the dimension of rod 104 with firm upward pressure into the space between the jaws 112 and 114 will engage inwardly facing, opposed surfaces 116 and 117 of jaws, resiliently spread the jaws apart, and move into opening 115; at which time the spreading pressure on the jaws will be released, causing the jaws to close around the rod and retain it in place.

The lower frame section 42, in a preferred embodiment, is identical to the upper frame section 40. Accordingly, for the sake of brevity, the components of the lower section 42 will be referenced herein and in the drawings with the same reference numerals as for the upper section 40, with the inclusion of a prime suffix.

Returning now to FIGS. 1 and 5 in particular, it will be seen that in the assembled frame 39, male hinge component 96 mates with female hinge component 98' and that female hinge component 98 mates with male hinge component 96' to hingedly couple the upper U-shaped member 40 to the lower U-shaped member 42. That is, the male component 96 is snap fit into the female component 98' by inserting rod 104 of the component 96 into opening 116' provided between jaws 112' and 114' of the female component 98', as described above. Similarly, the male component 96' is snap fit into the female component 98 by inserting rod 104' of the component 96' into opening 116 provided between jaws 112 and 114 of the female component 98. Mating of the couplings may be accomplished simultaneously or one at a time.

When coupled, the upper section 40 and the lower section 42 are positioned adjacent one another for hinged rotation relative to one another about pivot axis X, as shown by the arrow F. In one direction (clockwise as viewed in FIG. 4), rotation of the sections 40 and 42 is limited by engagement of the end edges 79 and 79' of the front panels 54 and 54'; this being referred to as the "closed" position of the frame shown in FIGS. 1 and 2. To this end, it will be understood that rotation is limited because the end edges 79 and 79' together with webs 84 and 84' provide relatively broad and rigid contact surfaces which meet and cannot pass by one another when the articulator is in its closed position. It is also to be noted that in the closed position, the length axes of channels 74 and 74' are generally coaxially disposed along a line generally perpendicular to the pivot axis X and the occlusal plane P. Also, it will be realized that pivotable movement of frame sections 40 and 42 about hinge axis X sweeps the length axes of the channels 74 and 74' through arcs which lie in a plane disposed generally perpendicular to the hinge axis and to the occlusal plane.

To further enhance the limiting feature of the articulator and for other advantages, raised protuberances 118, 118', 120 and 120', each having a height of about 1/64 inch, a width of about 1/16 inch and a length of about 1/4 inch may be co-formed or otherwise provided on the end edges 79 and 79' of front panels 54 and 54', respectively, extending from opposite sides of the webs 84 and 84'.

The protrusion members 44 and 46 are preferably of identical construction. Accordingly, the components of the protrusion member 44 will be described in detail with the same reference numerals applied to the protrusion member 46 with the inclusion of a prime suffix.

With reference now to FIGS. 7a–7e, the protrusion member 44 is preferably of one-piece molded plastic construction including a substantially hemispherical head 122, a neck 124 extending from the head, base 126 extending outwardly from the neck, and a pin 128 projecting downwardly from the base 126.

Figure 7A:
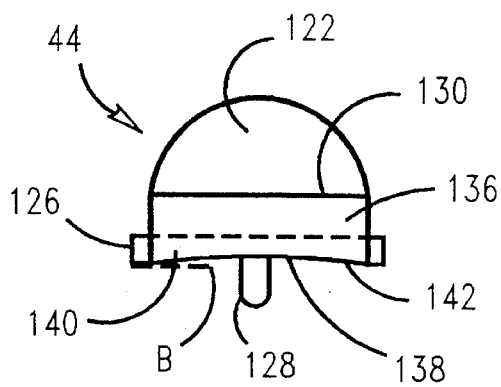
FIGS. 7a–7e are front, rear, left-side, top and bottom views, respectively, of one of a protrusion member of the articulator.
Figure 7B:
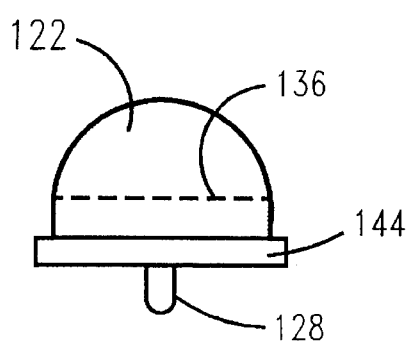
Figure 7C:
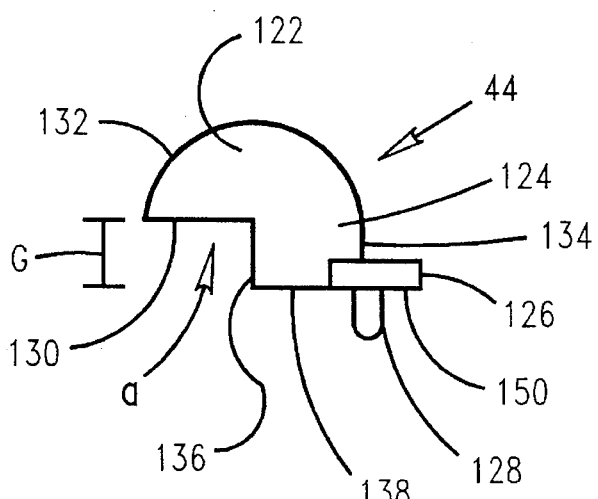
Figure 7D:
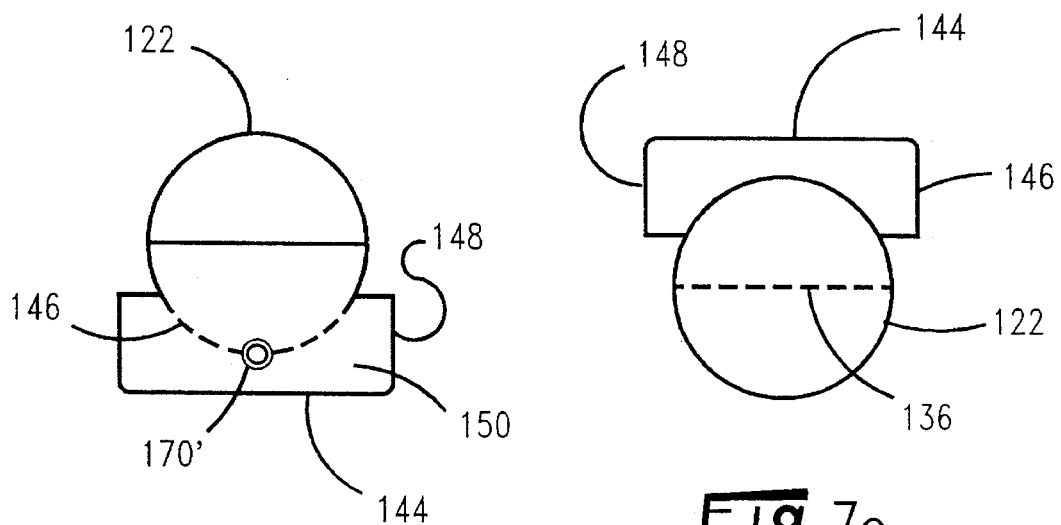
Figure 7E:
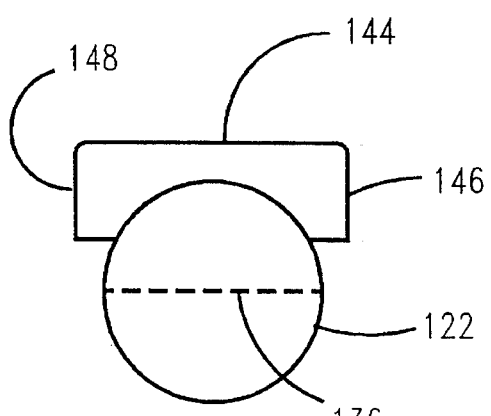

In a preferred embodiment, the head 122 includes a medial flat surface 130 and a hemispherical upper surface 132 having a radius substantially equal to that of the channel recess 74 of the frame section 40. The neck 124 extends downwardly from approximately the equatorial line of upper surface 132. The neck 124 has a substantially semi-circular cross-section viewed as shown in FIG. 7e, with a radius substantially equal to that of the head, and a nominal thickness G as shown in FIG. 7c of about 1/8 inch. The neck 124 therefore includes a cylindrical outer surface 134, a substantially flat interior surface 136 and also a slightly angled lower surface 138 shown in FIG. 7a.

The outer surface 134 of neck 124 is preferably substantially tangent to the outer surface 132 of the head 122. The angled lower surface 138 may have opposed sloping sides 140 and 142, each side 140 and 142 sloping outwardly with respect to horizontal at an angle β of between about 1° and 10° and meeting at about the midline of the member 44.

The base 126 is substantially planar as viewed from the top (FIG. 7e) and may have a thickness of about 1/16 inch. The base 126 extends normally from the curved surface 134 of the neck 124 and includes a substantially straight back edge 144, side edges 146 and 148, and lower surface 150. Back edge 144 may have a length of about 11/16 inch and is oriented substantially parallel to the surface 132 of the neck 124. The side edges 146 and 148 are substantially parallel and are located at opposite ends of the back edge 144 with the lower surface 150 generally even and continuous with the lower surface 138 of the neck 124.

The pin 128 projects from a central location on the lower surface 150 of base 126 and is sized to be received within a channel 48 or other opening provided in the cast 14. In a preferred embodiment, the pin 128 has a length of about 3/16 inch and is rounded with a blunt end, having a diameter of about 1/8 inch.

Assembly of the dental model 10 provides a dental model 10 which realistically simulates occlusion and desired occlusal and masticatory movements of the casts 14 and 16. According to a preferred embodiment of the method of the present invention, as illustrated in FIGS. 8a–8f, and with continuing reference to FIG. 5, the dental model 10 may be assembled by providing the casts 14 and 16 according to well-known techniques and securing the articulator 12 to the casts to support the casts 14 and 16 in the desired manner. As mentioned above, the cast 14 includes base 18, gum area 20 and teeth 22 and the cast 16 includes base 24, gum area 26, teeth 28 and bridge 30. The base 18 may have a flat rear surface 152 and a curved front surface 154 and may be prepared for receiving the protrusion member 44 by forming the channel 48 or other indentation on the medial area of the rear surface 152. Similarly, the base 24 of the cast 16 may have a flat rear surface 156 and a curved front surface 158 and may be prepared for receiving the protrusion member 46 by forming the channel 50 on the medial area of the rear surface 156 of the cast 16.

The prepared casts 14 and 16 (FIG. 8a) are positioned by the technician in occlusion with the opposing surfaces of the teeth in contact with one another in proper bite registry above and below occlusal plane P and are maintained in occlusion, as by use of a clamp but preferably and most expeditiously by application of gentle but firm pressure by the hand of the dental technician assembling the model 10.

With the casts 14 and 16 supported in occlusion, the pins 128 and 128' of the protrusion members 44 and 46 may then be adhesively secured, preferably one at a time, within the channels 48 and 50 of the casts 14 and 16, respectively. For example, to secure protrusion member 44 to cast 14, a small amount of a quick-setting adhesive (e.g., cyanoacrylate) may be applied to the pin 128 and/or the channel 48 and the pin 128 is positioned to extend into the channel 48 with the lower surface 150 of the base 126 against the rear surface 152 of the base 18 such that the length axis of the base 126 is aligned with the length axis of the rear edge 152. Following this, an accelerator of a type well known in the art for a cyanoacrylate adhesive may be applied to the adhered area, as by spraying, to accelerate setting of the adhesive. Protrusion member 46 may be secured to cast 16 in a similar fashion, generally positioned in alignment with member 44 along line L (FIG. 8d) generally perpendicular to occlusal plane P.

With continued support of the casts 14 and 16 in occlusion, the surfaces 132 and 132' of head 122 and 122' are adhesively secured, preferably simultaneously, within the recesses 74 and 74' of the hingedly coupled upper and lower frame sections 40 and 42, respectively, with the frame sections in the closed position.

To secure the surfaces 132 and 132' within recesses 74 and 74', a small amount of a fast-setting adhesive (e.g., cyanoacrylate) may be applied to the surfaces 132 and 132' and/or the recesses 74 and 74', and the surfaces 132 and 132' are pressed firmly against the surfaces 74 and 74', respectively, until the adhesive has set. Again, an accelerator of a type well known in the art for cyanoacrylate adhesive may be applied to the adhered area, as by spraying, to accelerate setting of the adhesive.

It is important in assembly of the models with the articulator that the frame sections 40 and 42 be closed and oriented with their front panels 54 and 54' and the length axes of channels 74 and 74' substantially parallel to rear surfaces 152 and 156 of casts and generally perpendicular to occlusal plane P at the moment the frame sections are brought into contact with the surfaces 132 and 132', and that the technician hold the parts stationary with respect to one another from the moment of contact while the adhesive sets.

Figure 8A:
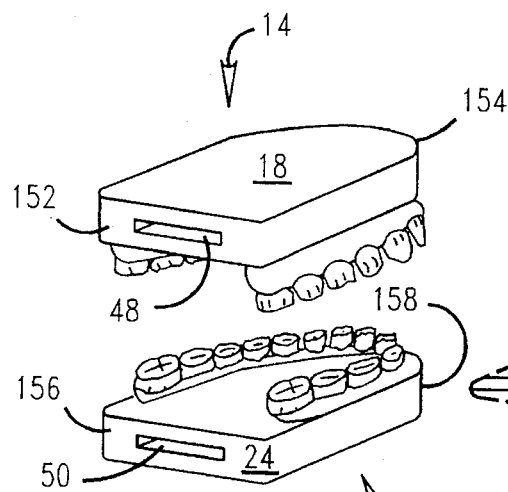
FIGS. 8a–8f show steps in a method according to the present invention.
Figure 8B:
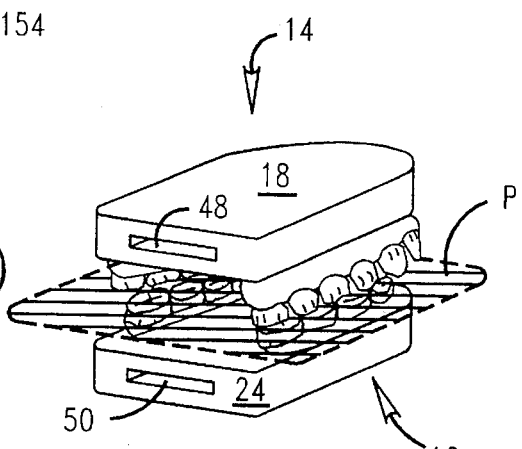
Figure 8C:
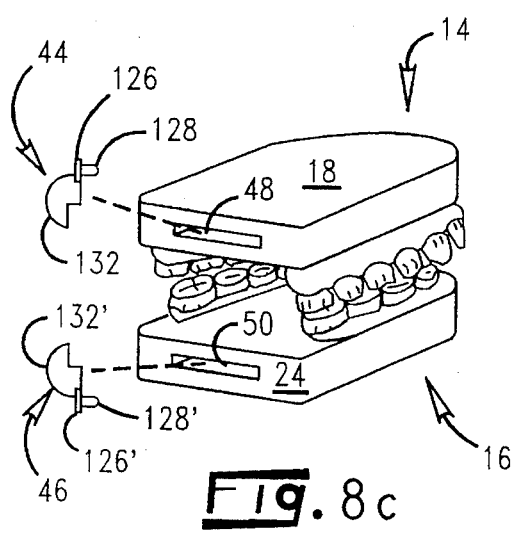
Figure 8D:
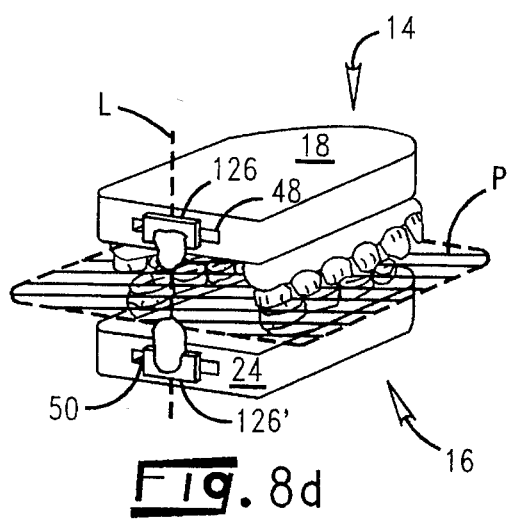
Figure 8E:
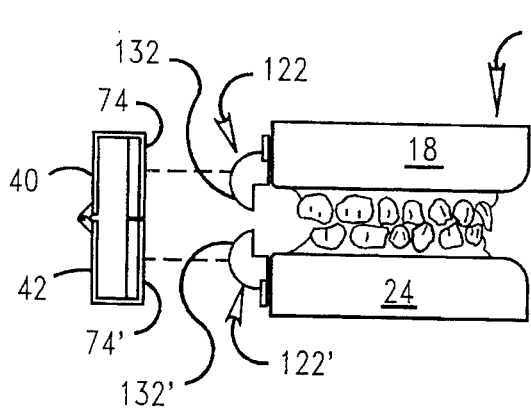
Figure 8F:
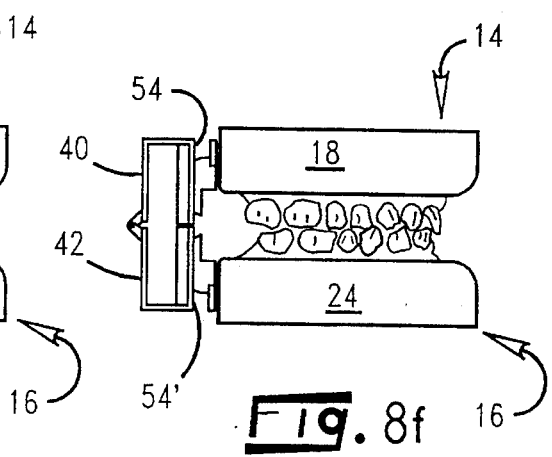

Once assembled, the model 10 shown in FIGS. 1 and 8f may be used to realistically simulate occlusion and occlusal and masticatory movements and to evaluate the compatibility of the bridge as previously discussed in connection with FIGS. 2, 3 and 4. This realistic reproduction of movements results in part from the configuration and size relationships of the various components of the articulator 10. For example, returning to FIGS. 3 and 4, a comparison of these figures shows that the articulator 12 may be deformed under application of forces to effect masticulatory movement. In this regard it will be understood that the nature of the deformation of the U-shaped members 40 and 42 causes forces acting on the articulator, such as those applied by the dental technician during evaluation of the bridge, to be diffused throughout the articulator so that the articulator absorbs the force and reduces the strain on the hinges to enable a wider range of simulated occlusal and masticatory movements of the casts 14 and 16 as compared to conventional articulators.

In addition, diffusion of force by the articulator results in occlusal and masticatory movement of the casts 14 and 16 which more closely resembles movement of the human mouth. This is advantageous to enable more accurate evaluation of the compatibility of the bridge 30.

Moreover, as mentioned previously with respect to FIGS. 3 and 4, the distance D between the front panel 54 and the rear panel 56 is greater in FIG. 3 than in FIG. 4 and the distance E between the front panel 54' and the rear panel 56' is less in FIG. 3 than in FIG. 4. This deformation of the panels 54, 54' and 56, 56' reduces the concentration of stress on the hinge components to enable a wider range of movement and yieldably resists and absorbs force so that responsive movement of casts 14 and 16 is smoother and more uniform.

Figure 9A:
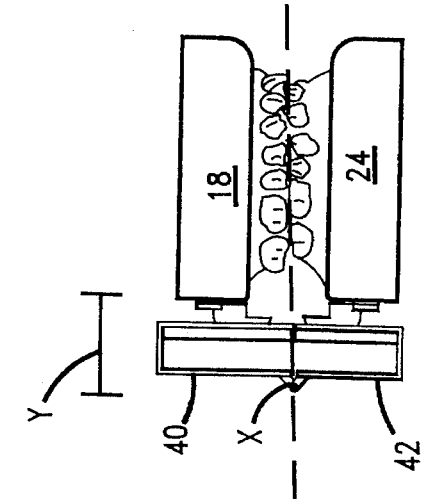
FIGS. 9a–9c show dental model casts mounted at various heights on the articulator of the present invention.
Figure 9B:
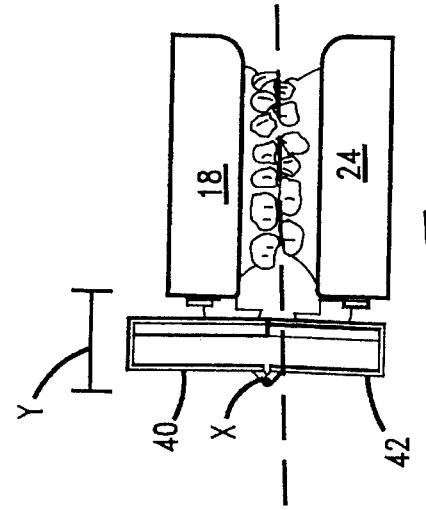
Figure 9C:
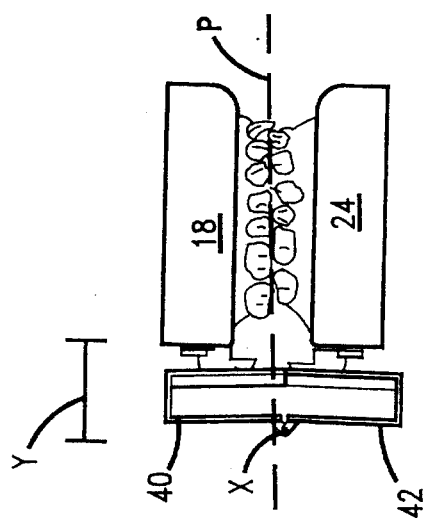

In addition to the advantage of more realistic simulation of occlusal and masticulatory movements with reduced likelihood of mechanical failure, the articulator of the present invention offers further advantages over conventional articulators, particularly conventional plastic disposable articulators. For example, with reference to FIGS. 9a to 9c, there is shown the articulator of the present invention having the dental model casts 12 and 14 mounted at various heights on the articulator. As can be seen, the position of the hinge axis relative to the occlusal plane P may be varied without changing the distance Y of the articulator from the casts. The distance Y is substantially the same in FIG. 9a as it is in FIG. 9b and FIG. 9c, however, the hinge axis X is above the occlusal plane P in FIG. 9b and is below the occlusal plane P in FIG. 9c.

Figure 10A:
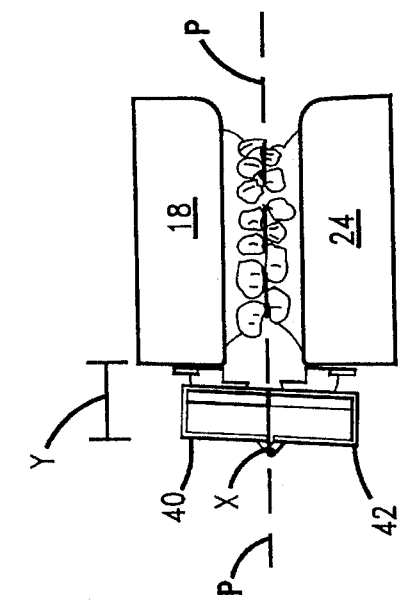
FIGS. 10a–10c show dental model casts of various thicknesses mounted on the articulator of the present invention.

Another advantage of the present invention is that the position of the hinge axis X and the distance Y is the same irrespective of the thickness of the cast or the height of the teeth. For example, with reference to FIGS. 10a to 10c, the articulator 12 is shown having thick casts mounted thereon (FIG. 10a), normal casts (FIG. 10b) and small casts (FIG. 10c). As can be seen, the distance Y is substantially the same in each case.

These and other advantages stem from the elongate channels 74 and 74' which accommodates a significant range of variation in the dimensions and placement of the casts without affecting the rearward spacing of hinge axis X.

Figure 10B:
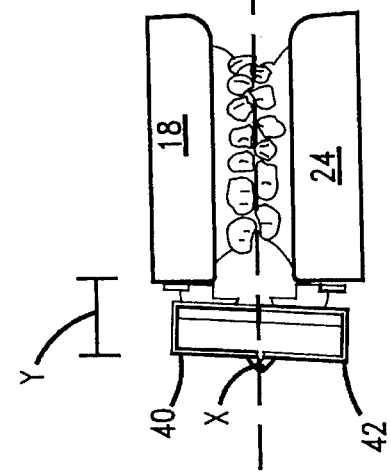
Figure 10C:
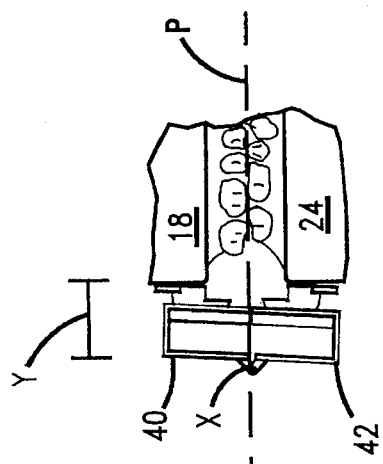
Figure 11A:
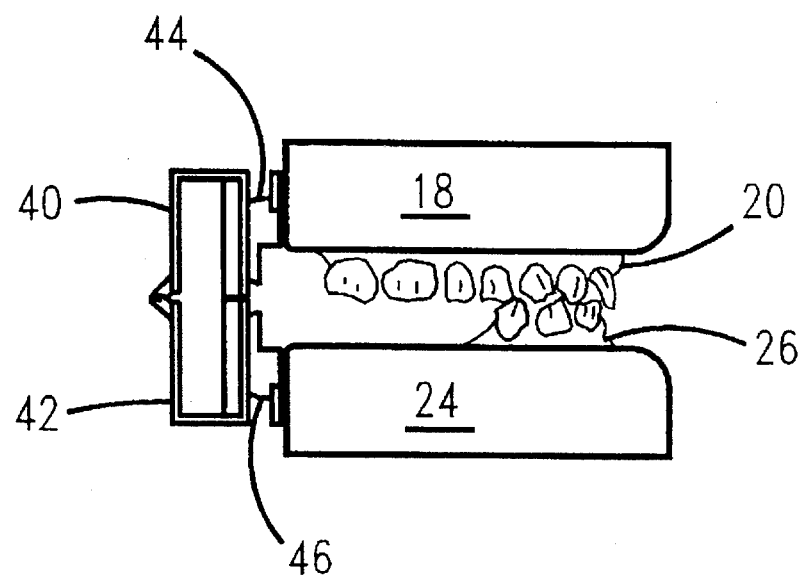
FIG. 11a shows a dental model cast having missing teeth mounted on the articulator and FIG. 11b shows dental model casts mounted in a spaced apart relationship.
Figure 11B:
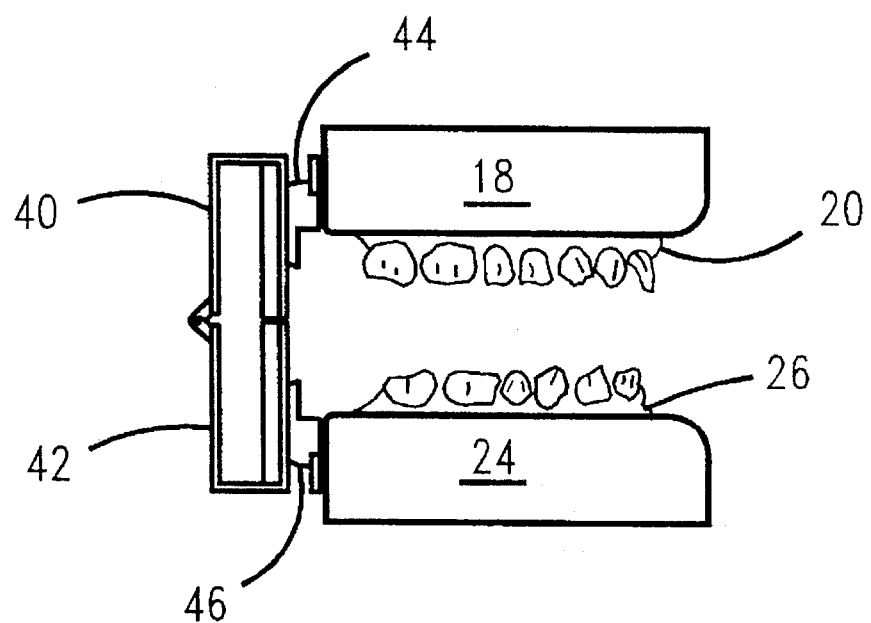

Another advantage of the articulator of the present invention over prior art articulators is that the articulator may be used to mount casts having missing teeth (FIG. 11a) or to mount the casts in a spaced apart relationship (FIG. 10b). Many prior art articulators are unable to support casts having missing teeth, particularly missing rear or wisdom teeth, in the occlusion position. When a dental model cast missing a section of back teeth is supported with a prior art articulator such as those shown in U.S. Pat. Nos. 4,382,787 and 4,449,930, the casts are not supported and tend to pivot or rotate toward one another in the area of the missing teeth. As can be seen in FIG. 11a, the articulator 12 of the present invention permits the teeth to be mounted in occlusion despite the fact that some of the rearwardmost teeth in the cast 14 are missing. Likewise, it is difficult to mount the casts in a spaced apart relationship with conventional articulators. However, as can be seen in FIG. 11b, this is easily accomplished using the articulator of the present invention.

The foregoing description of preferred embodiments of the present invention are given by way of illustration only. In light thereof, those of ordinary skill in the art will appreciate that numerous modifications, substitutions, omissions and rearrangements may be made without departing from the spirit and scope of the present invention as set forth in the claims.

We claim:

1. An articulator for supporting a pair of upper and lower dental models in occlusion and for simulating occlusal and masticatory movements of the dental models by application of an external force to the dental models said articulator comprising:

a first generally U-shaped member having a middle panel and integral front and rear panels spaced apart from one another and extending parallel to one another from opposite sides of said middle panel, said front panel having an elongate channel defined therein, said U-shaped member being resiliently deformable to substantially uniformly resist a force applied thereto so that the front and rear panels flex relative to one another upon application of the force thereto;

a second generally U-shaped member having a middle panel and integral front and rear panels spaced apart from one another and extending generally parallel from opposite sides of said middle panel of said second U-shaped member, said front panel of said second U-shaped member having an elongate channel defined therein, said second U-shaped members being resiliently deformable to substantially uniformly resist a force applied thereto so that the front and rear panels of said second U-shaped member flex relative to one another upon application of said second mentioned force thereto;

hinge means for hingedly securing the rear panel of said first U-shaped member to the rear panel of said second U-shaped member to enable the desired occlusal movement about a hinge axis;

limiting means defined on the front panels of said first and second U-shaped members for limiting movement of the first and second members of the articulator toward one another beyond a closed position at which the length axes of the channels are substantially coaxial;

a first protrusion member having a first surface positionable adjacent to and configured to mate with and to be adhesively securable to at least a portion of the channel of the front panel of the first U-shaped member and a second surface positionable adjacent to and adhesively securable directly to at least a portion of the upper dental model and a second protrusion member having a first surface positionable adjacent to and configured to mate with and to be adhesively securable to at least a portion of the channel of the front panel of the second U-shaped member and a second surface positionable adjacent to and securable directly to at least a portion of the lower dental model, each of said first and second protrusion members being of one-piece molded substantially rigid construction.

2. An articulator for supporting a pair of upper and lower dental models in a predetermined relationship for being forcibly manipulated out of the predetermined relationship by a user to simulate masticatory movements and adapted to cause the dental models to return substantially to the predetermined relationship when the force is withdrawn, the articulator comprising:

a frame comprising an upper half and a lower half and hinge means hingedly connecting said upper and lower halves together for pivotal movement with respect to one another about a hinge axis;

each of said upper and lower halves of said frame including a front section disposed generally in a front plane for being positioned adjacent a pair of dental models and a rear section disposed generally in a rear plane for being positioned distally of the dental models and bridge means for supporting said front and rear sections in spaced-apart relation;

said rear sections of said frame halves each having a pivot end spaced from said bridge means and said hinge means hingedly connecting said upper and lower halves together adjacent their respective pivot ends;

said front sections of said frame halves each having a stop end spaced from said bridge means and spaced from said pivot axis, said stop ends configured to engage one another at a closed position of said frame halves at which said front planes of said front sections are generally parallel to limit pivotal movement of said frame halves with respect to one another about said hinge axis beyond said closed position;

each of said front sections of said upper and lower frame halves including an elongate channel extending generally along a channel axis, the channels being disposed such that their respective channel axes are located in a channel plane disposed generally perpendicular to said hinge axis, and such that their respective channel axes are substantially coincident when said frame halves are in said closed position;

a pair of upper and lower one-piece molded protrusion members directly mountable upon the upper and lower dental models, the upper protrusion member including a protrusion matingly receivable and vertically positionably within the channel of the upper frame half at any desired position along the length of the channel and the lower protrusion member including a protrusion member matingly receivable and vertically positionable within the channel of the lower frame half at any desired position along the length of the channel;

means for fixedly connecting said upper and lower protrusion members directly to their associated dental models;

means fixedly connecting said protrusions of said upper and lower protrusion members to their associated frame halves with said protrusions matingly received in said channels with said dental models in their predetermined relationship; and said frame halves each being of an integral construction of a resiliently flexible material so that application of a force to said front section of one of said frame halves directed generally parallel to the front plane associated therewith causes said front section to be resiliently defected in relation to said rear section generally about said bridge means from a relaxed position at which said front and rear planes are generally parallel with said frame halves supporting the dental models in the predetermined relationship to a flexed position at which said front and rear plane are generally non-parallel and with said frame halves supporting the dental models out of their predetermined relationship, and to return substantially to said relaxed position when said flex force is withdrawn to cause the dental models to return to their predetermined relationship.

3. An articulator for supporting an upper and a lower dental model in a predetermined relationship above and below an occlusal plane comprising:

an upper and a lower dental model;

upper and lower one-piece molded protrusion members, said upper protrusion member substantially immovably connected directly to the upper dental model and including a protrusion protruding generally away from the upper dental model and said lower protrusion member substantially immovably connected to the lower dental model and including a protrusion protruding generally away from the lower dental model;

a frame including a pair of resiliently flexible upper and lower frame halves hingedly interconnected for movement with respect to one another about a hinge axis, said upper frame including a front section disposed adjacent the dental cast with an elongate channel disposed along a channel axis, wherein said channel immovably matingly receives therein said protrusion of said upper protrusion member at a desired position along the length of said channel and said lower frame half including a front section disposed adjacent the dental cast with an elongate channel disposed along a channel axis, wherein said channel of said lower frame half immovably matingly receives said protrusion of said lower protrusion of member at a desired position along the length of the channel, said channel axes of said channels of said frame halves being coincidentally disposed along a channel line which is generally perpendicular to said hinge axis and said occlusal plane and substantially bisects said frame halves.

4. An articulator for assembling and supporting a pair of upper and lower dental models in desired occlusal relationship for simulation of occlusal and masticatory movements, comprising:

a frame comprising resiliently deformable first and second frame sections pivotably connected together for pivotal movement about a pivot axis, each of said frame sections including an elongate channel, said channels being arranged such that pivotal movement of said frame sections about said pivot axis sweeps the length axes of said channels through arcs in a plane disposed substantially perpendicular to said pivot axis, said channels being defined in front panels of said frame sections spaced from rear panels by bridge panels thereof, said frame sections being pivotably connected together along said rear panels and said means for limiting comprising depending free end edges of said front panels which interengage in said closed position;

means for limiting pivotal movement of said frame sections beyond a closed position at which the length axes of said channels are disposed substantially coaxially and substantially perpendicular to said pivot axis;

upper and lower one-piece molded protrusion members, each of said protrusion members having a first end which is attachable directly to each one of the first and second dental models, respectively, and each of said protrusion members having a second end opposite said first end of said protrusion member, said second ends being dimensioned to matingly engage said first and second channels, respectively, and adhesively securable thereto at desired positions along the length of said channels with said frame sections in said closed position.

5. The articulator of claim 4, wherein said channels are of a round-bottomed configuration along their length axes with a generally uniform radius of curvature extending along the length thereof.

6. The articulator of claim 4, wherein said protrusion members are generally hemispherical.

7. The articulator of claim 4, further comprising a web disposed across said channels at their ends adjacent said pivot axis for limiting drainage of a liquid adhesive out of said channel.

8. A method of assembling upper and lower dental models in occlusion for simulation of occlusal and masticatory movements of the models in relation to one another, comprising:

placing the upper and lower dental models in occlusal relation so that an occlusal plane is established between the models;

attaching a one-piece molded protrusion member directly to each model so that the protrusion members are non-movably secured to the casts so that they are aligned generally along a line perpendicular to the occlusal plane;

providing a frame having resiliently deformable upper and lower frame sections pivotally connected together for pivotal motion about a pivot axis, each frame section defining an elongate channel, each of said channels being configured to matingly receive a protrusion member at a desired position along the length of the channel, the channels being disposed so that pivotable movement of the frame sections about the pivot axis sweeps the length axes of said channels through arcs lying in a plane generally perpendicular to the pivot axis, and the frame including means for limiting rotation of the frame sections relative to one another beyond a closed position at which the channels are disposed with their length axes generally along the same line;

placing the frame sections in their closed position against the protrusion members attached to the dental models in an aligned position with the protrusion member attached to the upper dental model received in the channel of the upper frame section and the protrusion member attached to the lower dental model received in the channel of the lower frame section and the pivot axis generally parallel to and generally in the plane of the occlusal plane; and securing the frame sections in their aligned position to the protrusion members.

9. The method of claim 8, wherein the frame sections are secured in their aligned position to the protrusion members by applying a quick-setting adhesive to the protrusion members and/or to the channels prior to placing the protrusion members against the channels and precluding relative movement between the protrusion members and the channels after they are brought into contact to facilitate setting of the adhesive with the frame sections in their aligned position.

10. The method of claim 8, wherein the line along which the length axes of the channel are disposed in the closed position of the frame is generally perpendicular to the occlusal plane.

11. The method of claim 8, wherein the frame sections are secured in their aligned position to the protrusion members by applying a quick-setting adhesive to the protrusion members and/or to the channels prior to placing the protrusion members against the channels and precluding relative movement between the protrusion members and the channels after they are brought into contact to promote setting of the adhesive with the frame sections in their aligned position, and further comprising blocking any drainage of adhesive along the channels by providing a web across the end of each channel closest to the pivot axis.

12. The method of claim 8, further comprising maintaining the frame sections in the aligned position while they are secured to the protrusion members.

13. A method for providing a dental model in occlusion for simulation of occlusal and masticatory movements, comprising the sequential steps of:

providing a pair of dental casts corresponding to the upper and lower sets of teeth of a human mouth, each of said casts having a rear surface;

providing an articulator, said articulator comprising:

a pair of resiliently deformable generally U-shaped members, each member having a middle panel and front and rear panels spaced apart from one another and extending downwardly in parallel relation from opposite sides of said middle panel, said members pivotally connected together along said rear panels for pivotable movement about a pivot axis, each of said front panels defining an elongate channel disposed generally perpendicular to the pivot axis, and a pair of one-piece molded protrusion members, each protrusion member having a first surface positionable adjacent to and configured to mate with and to be adhesively securable to at least a portion of one of the channels and a second surface positionable adjacent to and adhesively securable directly to at least a portion of one of the dental molds;

positioning the casts in occlusion so that opposing surfaces of the teeth are in contact with one another along an occlusal plane;

adhesively securing the second surface of one of the protrusion members directly to the rear surface of one of the dental molds while maintaining the casts in occlusion;

adhesively securing the second surface of the other one of the protrusion members directly to the rear surface of the other one of the dental molds while maintaining the casts in occlusion;

adhesively securing the first surface of each of the protrusion members directly to one of the channels while maintaining the casts in occlusion with the channels disposed with their length axes substantially coaxially along a line perpendicular to the occlusal plane.

* * * * *

UNITED STATES PATENT AND TRADEMARK OFFICE
CERTIFICATE OF CORRECTION

PATENT NO. : 5,482,460
DATED : Jan. 9, 1996
INVENTOR(S) : Robert P. Farnor, Jr. and David G. Scruggs It is certified that error appears in the above-indentified patent and that said Letters Patent is hereby corrected as shown below:

Col. 11, line 47, after "therein, said second U-shaped", delete "members" and insert --member--.

Signed and Sealed this

Thirteenth Day of August, 1996

Attest:

BRUCE LEHMAN

*Attesting Officer*    *Commissioner of Patents and Trademarks*